(«12») United States Patent
Maciejewski et al.

(10) Patent No.: US 8,905,277 B2
(45) Date of Patent: Dec. 9, 2014

(54) CABLE TRANSPORT CARRIER FACILITY AS WELL AS A SYSTEM WITH A MEDICAL IMAGING FACILITY AND A CABLE TRANSPORT CARRIER FACILITY

(75) Inventors: Bernd Maciejewski, Markt Erlbach (DE); Jörg Christopher Stapf, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 160 days.

(21) Appl. No.: 13/185,827

(22) Filed: Jul. 19, 2011

(65) Prior Publication Data

US 2012/0018593 A1 Jan. 26, 2012

(30) Foreign Application Priority Data

Jul. 22, 2010 (DE) .......................... 10 2010 031 944

(51) Int. Cl.
*B60R 9/055* (2006.01)
*G01R 33/28* (2006.01)
*B60R 9/045* (2006.01)
*B60R 9/058* (2006.01)
*B60R 9/048* (2006.01)
*B65D 85/68* (2006.01)
*A61B 5/055* (2006.01)
*G01R 33/38* (2006.01)

(52) U.S. Cl.
CPC ............... *G01R 33/28* (2013.01); *B60R 9/045* (2013.01); *B60R 9/058* (2013.01); *B60R 9/048* (2013.01); *B60R 9/055* (2013.01); *A61B 5/055* (2013.01); *B65D 85/68* (2013.01); *B65D 2585/86* (2013.01); *G01R 33/3802* (2013.01)

USPC .............................. 224/319; 224/328; 248/65

(58) Field of Classification Search
CPC .............. B60R 9/04; B60R 9/08; B60R 9/10; B60R 9/055; B60R 9/058; B60R 9/045; B60R 9/0425; B60R 3/007
USPC ............... 229/164, 174, 100; 224/42.39, 309, 224/310, 311, 315, 316, 319, 321, 322, 324, 224/328, 329, 330, 906, 929; 174/92; 248/49, 53, 65, 74.3, 56, 58, 61, 68.1, 248/544, 690
See application file for complete search history.

(56) References Cited

U.S. PATENT DOCUMENTS

| 5,133,489 | A | * | 7/1992 | Loew et al. ................. 224/42.39 |
| 5,639,048 | A | * | 6/1997 | Bartholomew et al. .......... 248/49 |
| 6,116,547 | A | * | 9/2000 | Johnson et al. ................. 248/49 |
| 6,371,343 | B1 | * | 4/2002 | D'Souza ........................ 224/324 |
| 6,375,068 | B2 | * | 4/2002 | Jackson et al. ................. 229/174 |
| 6,604,675 | B2 | * | 8/2003 | Southwell ..................... 229/164 |
| 7,381,899 | B2 | * | 6/2008 | Pfluger ........................... 174/92 |
| 7,845,528 | B2 | * | 12/2010 | McMillan ..................... 224/328 |
| 2003/0196922 | A1 | | 10/2003 | Reaux |
| 2007/0290100 | A1 | * | 12/2007 | Caveney ...................... 248/74.3 |
| 2008/0191436 | A1 | * | 8/2008 | Galgano et al. ............ 280/47.11 |
| 2009/0308902 | A1 | * | 12/2009 | Rex ............................... 224/315 |
| 2011/0303711 | A1 | * | 12/2011 | McMillan ..................... 224/310 |

* cited by examiner

*Primary Examiner* — Tan Le

(57) ABSTRACT

A cable transport carrier facility is proposed. The cable transport carrier facility is designed for transport of system cables installed on a medical imaging facility and is able to be installed on the medical imaging facility. The cable transport carrier facility has at least one component which is made at least partly of an organic material.

10 Claims, 5 Drawing Sheets

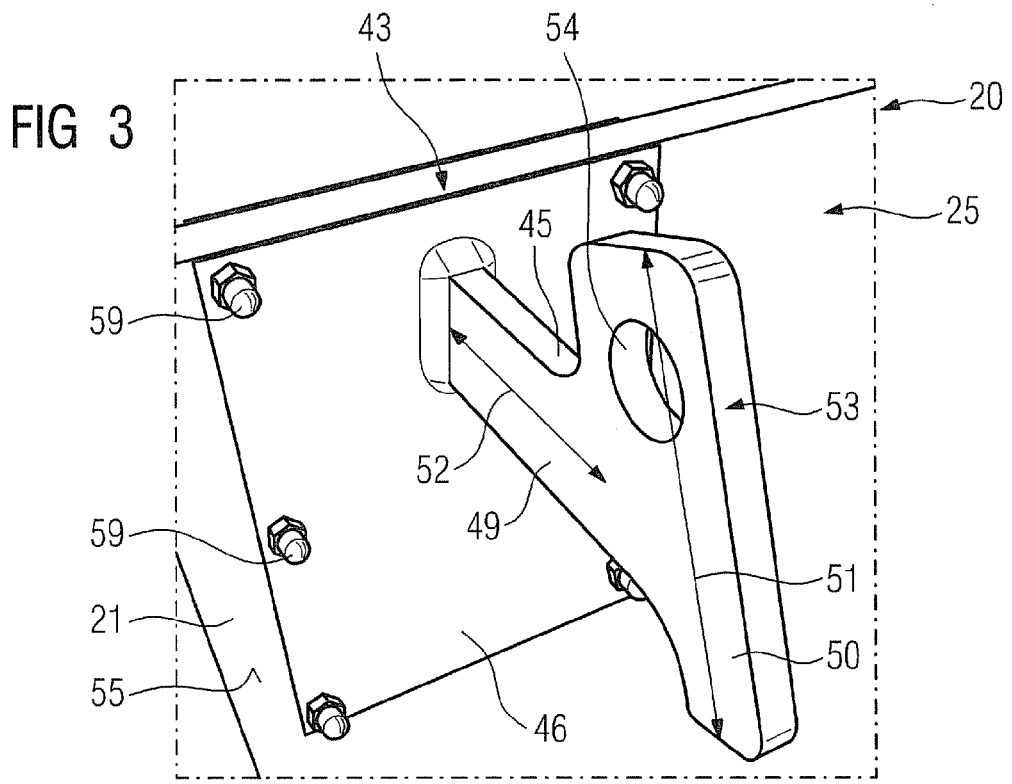
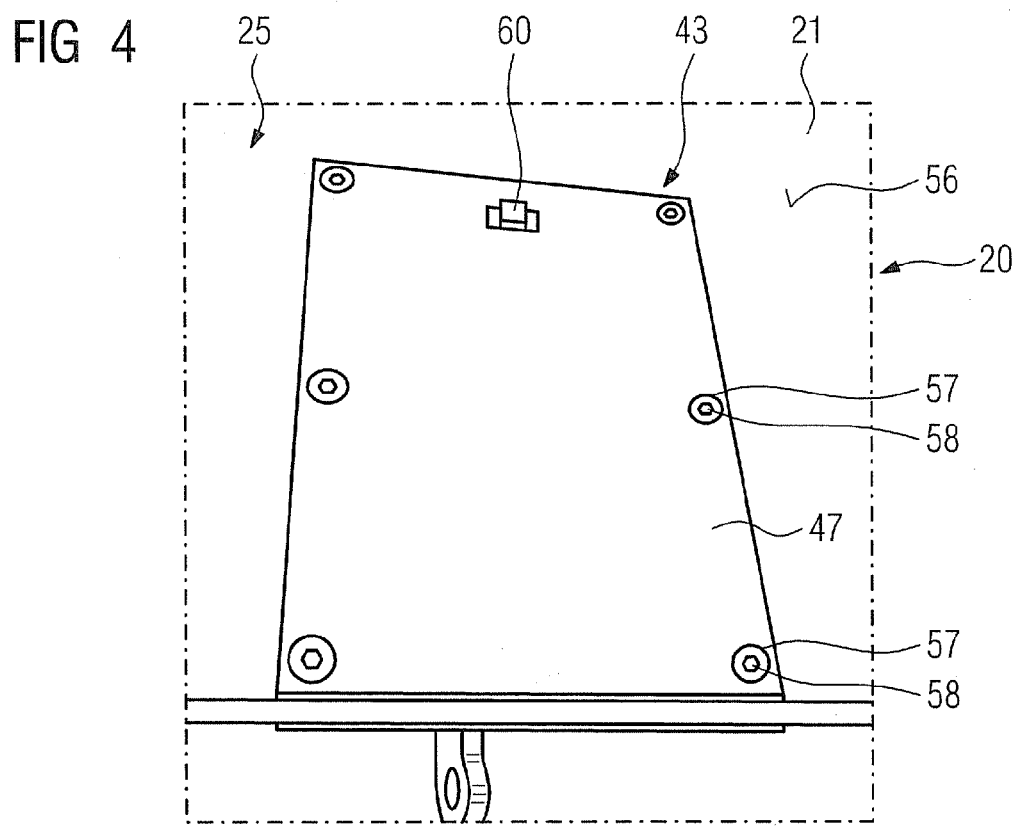

CABLE TRANSPORT CARRIER FACILITY AS WELL AS A SYSTEM WITH A MEDICAL IMAGING FACILITY AND A CABLE TRANSPORT CARRIER FACILITY

CROSS REFERENCE TO RELATED APPLICATIONS

This application claims priority of German application No. 10 2010 031 944.9 filed Jul. 22, 2010, which is incorporated by reference herein in its entirety.

FIELD OF THE INVENTION

The present invention relates to a cable transport carrier facility which is designed to transport system cables installed on a medical imaging facility and is able to be installed on the medical imaging facility for this purpose.

BACKGROUND OF THE INVENTION

A medical imaging facility, such as a magnetic resonance device for example, is constructed from a plurality of electronic components. The individual electronic components of the magnetic resonance device are connected to each other by means of system cables. In addition these electronic components are also connected by means of the system cables to units and/or components which are arranged outside a high-frequency cabin. These system cables are typically formed by electric cables and/or by optical waveguides.

These system cables are already installed on the magnetic resonance device prior to any transport of the magnetic resonance device. While the magnetic resonance device is being transported, especially to a location where the magnetic resonance device is used, the system cables must thus be transported together with a magnetic resonance device. Because of the plurality of system cables, which can constitute a weight of around 100 kg and more in total, an additional cable transport carrier facility is necessary however.

Thus for example a cable transport carrier facility for accommodating the system cables is known which is formed from a painted or powder-coated tubular steel profile. The cable transport facility is only used once however since the costs of return transport are very high. This known cable transport carrier facility thus has the disadvantage of high material costs.

SUMMARY OF THE INVENTION

The underlying object of the present invention is especially to provide a low-cost cable transport carrier facility which is especially easy to manufacture and which exhibits high stability. The object is achieved by the features of the independent claims. Advantageous embodiments are described in the dependant claims.

The invention is based on a cable transport carrier facility designed for transport of system cables installed on a medical imaging facility and which is able to be installed on the medical imaging facility for this purpose.

It is proposed that the cable transport facility has at least one component made at least in part of an organic material. The inventive cable support transport facility is designed to transport the system cables installed on the medical imaging facility together with the medical imaging facility during transport of the medical imaging facility, in which case neither the medical imaging facility nor the system cables are to suffer any undesired damage. The medical imaging facility is preferably formed by a magnetic resonance device or a computed tomography device. In this case system cables should especially be understood as electrical cables and/or optical waveguides and/or data transmission cables and/or further cables of the medical imaging facility which would appear sensible to the person skilled in the art. In particular the individual components of the medical imaging facility are connected by means of the system cables to further components and/or units which are located in a technical room, such as an amplifier etc. for example. Furthermore in this context an organic material is especially to be understood as a material having a basic structure with one or more carbon compounds. Preferably the organic material is formed by a material containing cellulose such as from a wood material and/or from a paper material for example, e.g. from a folding carton, so that in addition the cable transport carrier facility can be at least partly recycled. Furthermore the organic material can also be formed from a plastic material, especially from a polymer plastic material such as from an Acrylonitrile Butadiene Styrene copolymer and/or further materials appearing sensible to the person skilled in the art. An especially cost-effective cable transport carrier facility can be constructed by this embodiment. In addition the weight of the cable transport carrier facility can be reduced and at the same time a high stability of the cable transport carrier facility achieved, so that an especially simple assembly of the cable transport carrier facility is able to be obtained. Furthermore the cable transport carrier facility can be characterized by a high level of environmental friendliness, especially by an absence of coatings during the manufacturing of the cable transport carrier facility so that there are also low waste disposal costs after the cable transport carrier facility is transported together with the medical imaging facility to a usage location.

Furthermore it is proposed that the component has at least partly a support structure which is formed at least partly from the organic material. An advantageously high rigidity and/or stability of the cable transport carrier facility can be achieved in this way for the transport of the system cables together with the medical imaging facility.

In an advantageous development of the invention it is proposed that the cable transport carrier facility has a floor panel unit for accommodating the system cables of the medical imaging facility. The floor panel unit enables the weight of the system cables, which can be up to 100 kg and more, to be distributed evenly over the entire cable transport carrier facility and overstressing of individual components and/or units of the cable transport carrier facility can be prevented in this way.

Advantageously the floor panel unit is embodied such that it has at least one cutout through which especially system cables can be constructively easily passed for storage on the floor panel unit. Preferably the floor panel unit features a number of cutouts so that system cables from different directions and/or different positions can be routed through these cutouts for storage on the floor panel unit and in addition for example cable kinks and/or similar adverse effects on the system cables can be advantageously prevented.

In a further embodiment of the invention it is proposed that the cable transport carrier facility has at least one wall element for accommodating the system cables. An advantageous accommodation area for storing the system cables during transport of the medical imaging facility can be achieved, as can be especially advantageous during transport of sensitive optical waveguides.

Advantageously the wall element is arranged substantially perpendicularly to a floor panel unit on the latter. Substantially perpendicular is to be understood here as a main extent surface of the at least one wall element being aligned substantially perpendicular to a main extent surface of the floor panel unit. An advantageous storage area for the system cables can be achieved by this so that a secure storage of the system cables can be guaranteed during transport. Especially advantageously the cable transport facility features at least two or more wall elements which are each arranged substantially perpendicular to the floor panel unit on the latter, so that in addition stability of the cable transport carrier facility can be increased.

Preferably the at least one wall element also has at least one cutout and especially preferably a number of cutouts, so that here too system cables can be routed through these cutouts constructively simply for storage on the floor panel unit and/or cable attachment elements can be attached for securing the system cables. Advantageously the cutouts are embodied such that they can serve together with a wall area surrounding the cutouts of the at least one wall element as grip elements so that an especially convenient installation of the cable transport facility on the medical imaging facility can be achieved.

It is further proposed that the component is formed at least partly by the floor panel unit and/or the at least one wall element. In this case the floor panel unit is especially advantageously made of wood so that in addition sufficiently high stability for the transport of the heavy system cables can be achieved. Furthermore the floor panel unit can also be made of a raster core panel, which especially features a support structure made of polymer plastic. The at least one wall element can likewise be made of a wood and/or from a raster core panel and/or of board. This embodiment of the invention enables the cable transport carrier facility to be manufactured at especially low cost with high stability. Furthermore the cable transport carrier facility can be disposed of especially easily after use in that these components are formed substantially from recyclable materials. Embodying the floor panel unit and/or the at least one wall element from wood is further characterized by high environmental friendliness since wood is a renewable raw material and in addition a painted coating can be dispensed with.

It is further proposed that at least the floor panel unit and/or the at least one wall element be formed at least partly from a folding carton. For example the floor panel unit and the at least one wall element are formed in one piece in this process from a single folding carton so that an especially low-cost and simple cable transport carrier facility can be provided. In addition a higher level of environmental friendliness, especially as a result of dispensing with paint coatings, of the cable transport carrier facility can be achieved and thereby low-cost disposal after use of the cable transport facility can be achieved. The folding carton can be folded in this case such that high stability of the cable transport carrier facility can be achieved during transport of the medical imaging facility together with the cable transport carrier facility.

Especially advantageously further components and/or space and/or installation costs can be saved if the floor panel unit is embodied at least partly in one piece with the at least one wall element.

In an advantageous development of the invention it is proposed that the cable transport carrier facility has at least one support unit for supporting it on the medical imaging facility. Preferably the support unit is arranged for this purpose on the floor panel unit. The cable transport carrier facility preferably features two support units, so that there is an even distribution of the force from the cable transport carrier facility to a main magnet of a magnetic resonance device for example and a high stability of the cable transport carrier facility can be achieved.

An especially stable support of the cable transport carrier facility, especially during transport of the medical imaging facility, can be achieved if the support unit has at least one base element. Preferably the cable transport carrier facility is supported by said element on a main magnet of a magnetic resonance device for example, so that unwanted damage to a housing shell of the magnetic resonance device can be prevented.

If the base element is also embodied substantially in the shape of a T, stable support of the cable transport carrier facility can be achieved even during dynamic stresses, especially during the transport of the medical imaging facility. In addition a large support surface can be achieved by means of the T shape of the base element on the medical imaging facility, especially on a main magnet of a magnetic resonance device, and thereby stable positioning. Preferably the base element extends in the shape of a T away from the floor panel unit.

Especially advantageously the base element has at least one cutout which typically enables the element to be attached to transport and/or lifting eyes of the main magnet. This especially enables savings to be made in additional attachment elements for attaching the cable transport carrier facility to the main magnet.

In a further embodiment of the invention it is proposed that the support unit has at least one fitting element for attaching the support unit to the floor panel unit, by which a low-friction attachment between the support unit and the floor panel unit and also an advantageous distribution of force from the floor panel unit to the support unit can be achieved during the transport of the medical imaging facility together with the cable transport carrier facility. Preferably the fitting element has a large contact surface for contact with the floor panel unit.

An especially compact cable transport carrier facility can be achieved if the base element is at least partly embodied in one piece with the fitting element.

It is further proposed that the at least one fitting element has an attachment element for attaching at least one system cable. An advantageous securing of the system cables located in the cable transport carrier facility can be achieved. Preferably the at least one fitting element is arranged for this purpose on a side of the floor panel unit facing towards an area of the floor panel unit for accommodating the system cables.

An especially robust and stable attachment of the support unit to the floor panel unit and also an especially secure and load-resistant support of the cable transport carrier facility on the medical imaging facility, especially a main magnet of a magnetic resonance device, can advantageously be achieved if the support unit has at least two fitting elements which are arranged on opposing outer surfaces of the floor panel unit.

Advantageously the support unit has at least one connecting element for this purpose which attaches the at least one fitting element to the floor panel unit, which enables an especially secure and stable cable transport carrier facility to be manufactured. Especially advantageously both fitting elements are attached to the floor panel unit by means of the at least one connecting element.

It is further proposed that the support unit is made at least partly from a metal, by which an especially stable support unit can be achieved which even resists high stresses, especially during the transport of the medical imaging facility. The support unit can typically be formed here from a steel welded construction. Especially advantageously however the support unit is formed from aluminum, so that additionally an especially light and stable cable transport carrier facility can be provided. In addition an especially cost-effective support unit for the cable transport carrier facility can be provided if the support unit is manufactured for example in an aluminum extrusion method.

It is further proposed that the cable transport carrier facility has a further support unit which is embodied in the form of a web. Preferably the further support unit extends on a side of the floor panel unit facing away from an accommodation area for accommodating the system cables away from said unit in the form of a web so that advantageously additional support of the cable transport carrier facility can be achieved.

The invention is also based on a system comprising:
a medical imaging facility;
a cable transport carrier facility for transport of system cables installed on the medical imaging facility as claimed in one of the claims, with the cable transport carrier facility, for transport of the medical imaging facility, able to be mounted on the latter.

The invention is also based on a folding carton for manufacturing a cable transport carrier facility as claimed in at least one of the claims.

BRIEF DESCRIPTION OF THE DRAWINGS

Further advantages emerge from the description of the drawing given below. Exemplary embodiments of the invention are shown in the drawing. The drawings, the description and the claims contain numerous features in combination. The person skilled in the art will also consider the features individually and group them into sensible further combinations.

The figures show:

FIG. 3 a first part area of the support unit,

FIG. 4 a second part area of the support unit,

DETAILED DESCRIPTION OF THE INVENTION

Figure 1:
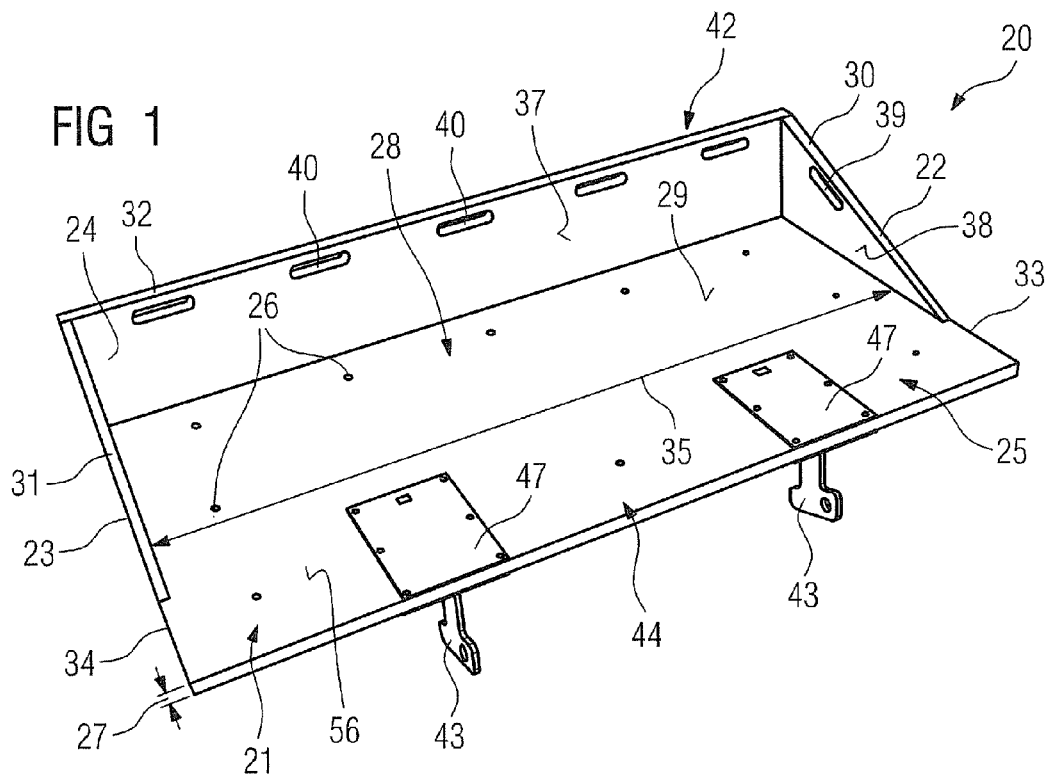
FIG. 1 an inventive cable transport carrier facility viewed from above.

FIG. 1 shows the inventive cable transport carrier facility 20. The cable transport carrier facility 20 is designed to accommodate system cables which are installed on a medical imaging facility 10 and have to be transported during the transport of the medical imaging facility 10 to a usage location together with the latter. The system cables in this case are preferably formed by electrical cables and/or lines and/or by optical waveguides and/or further cables and/or lines appearing sensible to the person skilled in the art. The system cables installed on the medical imaging facility 10 can have a weight of up to 100 kg and more in this case.

In the exemplary embodiment below the medical imaging facility 10 is formed by a magnetic resonance device. In an alternate embodiment of the medical imaging facility 10, said facility can also be formed by a computed tomography device.

The magnetic resonance device and the cable transport carrier facility 20 together form a system formed by a magnetic resonance system 1. The magnetic resonance system comprises a main magnet 12 which is surrounded by housing shells 13. The cable transport carrier facility 20 is supported or attached on and/or to this main magnet 12 such that damage to the housing shells 13 is prevented. The basic structure of the magnetic resonance device is known to the person skilled in the art, so that a more detailed description and presentation of the magnetic resonance device will be dispensed with below.

To accommodate the system cables of the magnetic resonance device the cable transport carrier facility 20 has a component 21 formed by a floor panel unit 25 which is made of an organic material containing cellulose, especially of wood (FIG. 1). The floor panel unit 25 has a number of cutouts 26 which extend through the entire width 27 of the floor panel unit 25 and are formed by holes open on both sides within the floor panel unit 25. These cutouts 26 are provided to have cable ties passed through them for attachment of system cables of the magnetic resonance device, so that these system cables can be secured constructively simply from the magnetic resonance device in an accommodation area 28 of the cable transport carrier facility 20 and in this way damage to the system cables, especially cable kinks, can be prevented. The individual cutouts 26 are embodied in the shape of cylinders in the present example and also in an even spacing from one another along a circumferential direction of a main extent surface 29 of the floor panel unit 25. Basically an alternate embodiment of the cutouts 26 and/or an alternate arrangement of the individual cutouts 26 in relation to one another in a further embodiment of the floor panel unit 25 is always conceivable.

Figure 5:
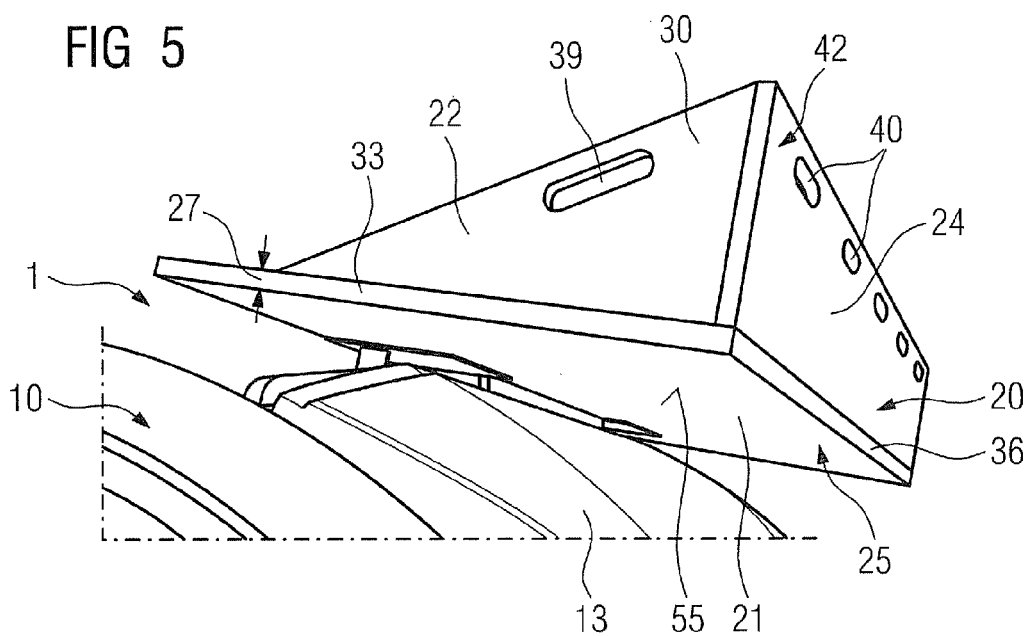
FIG. 5 the carrier unit in an installed position on a medical imaging facility.

Furthermore the cable transport carrier facility 20 features a number of wall elements 30, 31, 32 each formed by a component 22, 23, 24, which are likewise made of an organic and cellulose-containing material, especially from wood. The individual wall elements 30, 31, 32 are each aligned substantially perpendicular to the floor panel unit 25 and are arranged on the latter. Two of the wall elements 30, 31 are arranged on opposing transverse sides 33, 34 of the floor panel unit 25 and are each formed by one side element. The two side elements are arranged in this case along a longitudinal extent 35 of the floor panel unit 25 transverse to the latter on opposing transverse sides 33, 34 of the floor panel unit 25. In addition the two side elements are arranged substantially perpendicular to the third wall element 32 on the latter, so that the three wall elements 30, 31, 32 together with the floor panel unit 25 form an open accommodation area 28. The accommodation area 28 is embodied open in the direction of a side of the floor panel unit 25 which lies opposite the third wall element 32. Furthermore the accommodation area 28 is likewise embodied open on a side of the three wall elements 30, 31, 32 facing away from the floor panel unit 25. The third wall element 32 is arranged in this case on a longitudinal side 36 of the floor panel unit 25 (FIG. 5).

Figure 2:
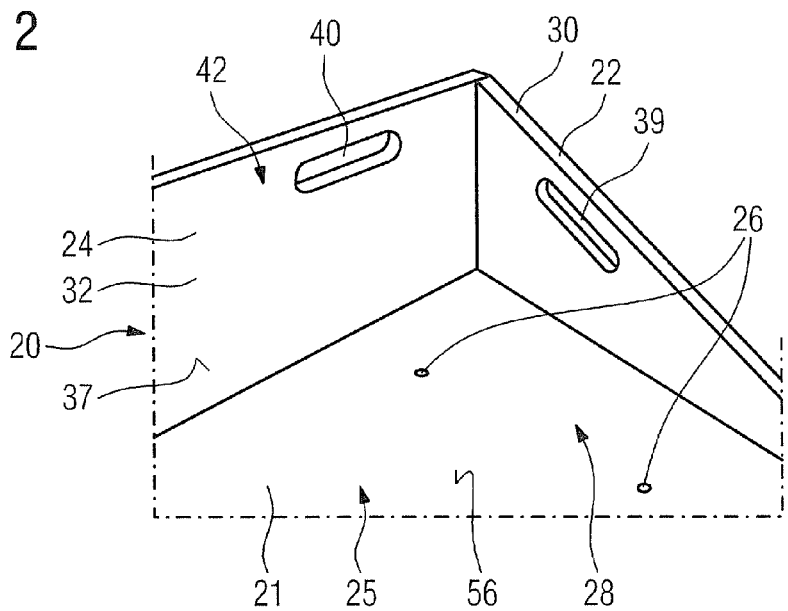
FIG. 2 a part area of the cable transport carrier facility.

The third wall element 32 has a substantially rectangular main extent surface 37 and the two side elements each have a substantially triangular main extent surface 38 (FIGS. 1 and 2). The two side elements each have a cutout 39 and the third wall element 32 has five cutouts 40, which extend through an entire thickness of the wall elements 30, 31, 32 and are intended for the system cables to pass through and/or for attaching the system cables by means of cable ties for example. The cutouts 39, 40 are each arranged in an edge area of the respective wall element 30, 31, 32 facing away from the floor panel unit 25. In addition the individual cutouts 39, 40 are substantially formed by rectangular holes with end areas embodied rounded, so that these cutouts 39, 40 together with a surrounding edge of the cutouts 39, 40 can be used as grips for the installation personnel during installation of the cable transport carrier facility 20 on the magnetic resonance device and thus simple installation of the cable transport carrier facility 20 can be achieved. In an alternate embodiment of the cable transport carrier facility 20 a number of the cutouts 39, 40 for the individual wall elements 30, 31, 32 and or a shaping of the individual cutouts 39, 40 can be embodied differently from the present exemplary embodiment.

The cable transport carrier facility 20 has two support units 43 for supporting the cable transport carrier facility 20 on a main magnet 12 of the magnetic resonance device, each of which is formed from a metal. The two support units 43 can be formed from a steel welded construction and/or especially advantageously from an aluminum and/or an aluminum alloy. The two support units 43 are arranged on an edge area 44 of the floor panel unit 25 adjacent to the third wall element 32 on the latter, as can be seen from FIGS. 1, 3 and 4.

The individual support units 43 each feature a base element 45, which is embodied in a T shape, and two fitting elements 46, 47. The base element 45 is embodied in one piece with one of the two fitting elements 46 and is arranged together with this on a side of the base plate element 25 facing away from the area 28 for accommodating the system cables. In this case the base element extends in the shape of a T away from the floor panel unit 25. An alternate embodiment of the support units 43, especially of the base element 45, is also conceivable, with the base element 45 preferably able to be adapted to a geometry of the magnetic resonance device, especially to a geometry of the main magnet 12 so that, depending on an embodiment of the magnetic resonance device, an effective support of the cable transport carrier facility 20 by means of the support units 43 is achieved.

FIG. 3 shows a more detailed diagram of a part area of the cable transport carrier facility 20 with a base element 45, comprising a first area 49, which extends in the form of a web away from the fitting element 46. This first area 49 is adjoined by a second area 50 of the base element 45, of which the longitudinal extent 51 is essentially transverse to a longitudinal extent 52 of the first area 49 of the base element 45. The fitting element 46 and the second area 50 are thus arranged at opposite end areas of the first area 49 along its longitudinal extent 52. The second area 50 comprises a contact surface 53 and/or a support surface, which is formed by a side of the second area 50 facing away from the floor panel unit 25. By means of this contact surface 53 and/or support surface the cable transport carrier facility 20 rests on the magnetic resonance device, especially on the main magnet 12 of the magnetic resonance device.

The second areas 50 of the two base elements 45 each have a cylindrical cutout 54 which is also arranged on a side of the second areas 50 facing away from the third wall element 32. The cutouts 54 are embodied as attachment elements, by means of which the cable transport carrier facility 20 can be installed on transport eyes of the main magnet 12 for example, so that while the magnetic resonance device is being transported together with the cable transport carrier facility 20, a secure and stable storage of the system cables is made possible and also damage to the system cables and/or the housing shell 13 of the magnetic resonance device is prevented.

The two fitting elements 46, 47 are each designed for attaching the support units 43 to the floor panel unit 25 (FIGS. 3 and 4). For this purpose the two fitting elements 46, 47 are arranged on opposing outer surfaces 55, 56 of the floor panel unit 25, with a first fitting element 46, which is embodied in one piece with the base element 45, being arranged on an outer surface 55 of the floor panel unit 25 facing away from the area 28 for accommodating the system cables. A second of the two fitting elements 47 is arranged on an outer surface 56 facing towards the area 28 for accommodating the system cables. The two fitting elements 46, 47 each have a large contact surface for contact with the floor panel unit 25.

In addition the two fitting elements 46, 47 of a support unit 43 each have holes 57 which are arranged in an edge area of longitudinal sides of the fitting elements 46, 47. These holes extend substantially transverse to the contact surface of the fitting elements 46, 47. A connection element 58 of the support unit which is formed by a screw is routed through these holes 57 in each case. On a side of the floor panel unit 25 and of the first fitting element 46 facing away from the area 28 for accommodating the system cables the connecting elements 58 are prevented from falling out by means of an inner thread. The inner thread in this case is arranged in a separate element which is formed by a nut 59. It is also conceivable for the inner thread to be able to be arranged directly in the holes 57 of the fitting elements 46, 47 or to be in the form of one or more welded-on nuts which are rigidly connected especially to an underside of the fitting element 46.

Those fitting elements 47 of the support units 43 which are arranged on the outer surface 47 of the floor panel unit 25 which faces towards the area 28 for accommodating the system cables have an attachment element 60 on a side facing away from the floor panel unit 25. This attachment element 60 is intended for attaching the system cables and to this end is made of plastic in the present exemplary embodiment. To attach the system cables said cables are especially attached by means of a cable tie to this attachment element 60, so that these system cables are attached securely and at least to an extent unshakably to the cable transport carrier facility 20 during transport of the magnetic resonance device. The attachment elements 60 for attaching the system cables in this case are each formed by a hook element, as can be seen in FIG. 4.

Figure 6:
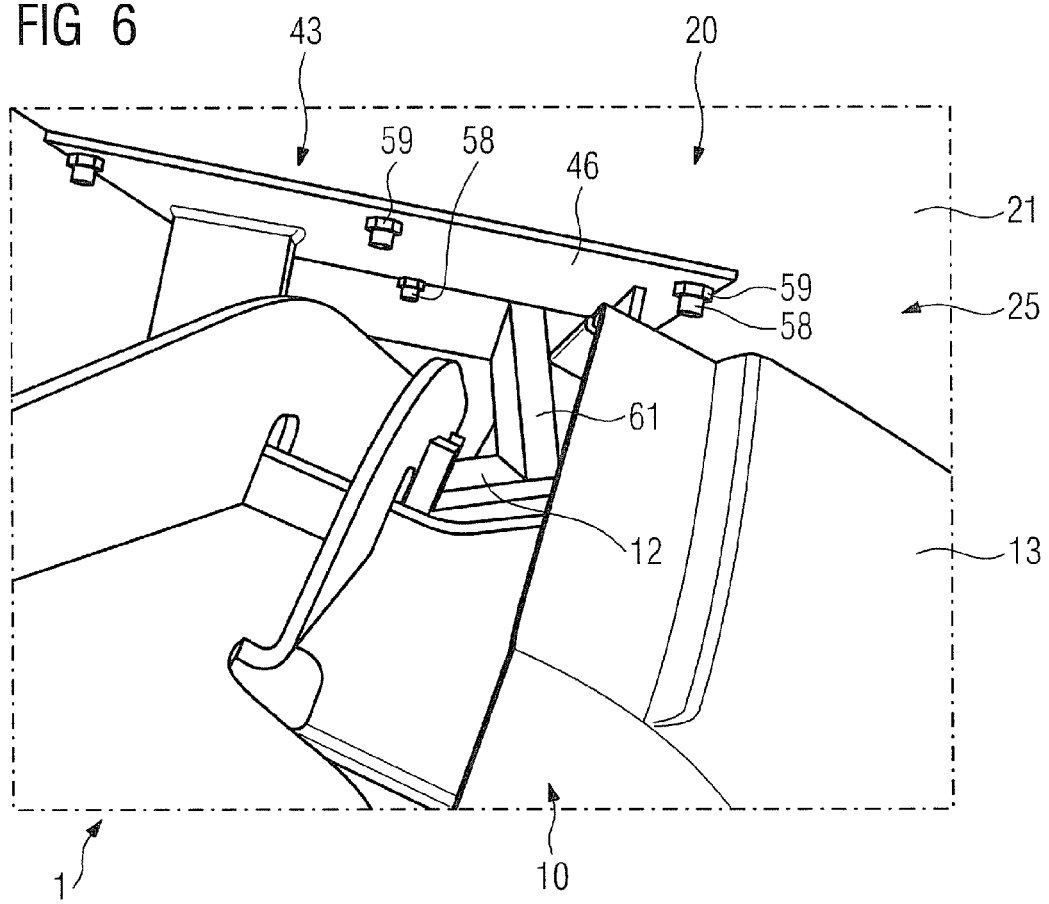
FIG. 6 a further diagram of the carrier unit in the installed position on the medical imaging facility, FIG. 7 an alternate embodiment of the cable transport carrier facility, FIG. 8 a folding carton for manufacturing the cable transport carrier facility from FIG. 8, FIG. 9 a floor panel unit for manufacturing the cable transport carrier facility from FIG. 8 and FIG. 10 a sectional view of a component with a support structure.

As can be seen from FIG. 6, the cable transport carrier facility 20 features a further support unit 61 which is arranged on the outer surface 46 of the floor panel unit 25 facing away from the area 28 for accommodating the system cables. This further support unit extends in the form of a web from the floor panel unit 25 and, in addition to the two first support units 43, supports the cable transport carrier facility 20 on the magnetic resonance device, especially on the main magnet 12 of the magnetic resonance device. This further support unit 61 is made of an organic material containing cellulose and especially of wood. The further support unit 61 is arranged along the transverse extent of the floor panel unit 25 in a direction from the two first support units 43 in the direction of the third wall element 32 after the two first support units 43 on the floor panel unit 25. In this direction the further support unit 61 makes an angle with the floor panel unit 25 which is less than 90°, so that an especially robust support of the cable transport carrier facility 20 on the magnetic resonance device during transport is achieved.

A part area of the magnetic resonance system 1 with the magnetic resonance device and the cable transport carrier facility 20 is shown in FIGS. 5 and 6. The magnetic resonance device comprises the main magnet 12, which has transport eyes not shown in greater detail for transporting the magnetic resonance device. The cable transport carrier facility 20 is installed by means of cutouts 54 of the two support units 43 by means of the transport eyes of the magnetic resonance device for transporting the magnetic resonance device. As can be seen from FIG. 6, the cable transport carrier facility 20 is held and/or supported by means of the three support units 43, 61 on the main magnet 12 of the magnetic resonance device such that the already installed housing shell 13 of the magnetic resonance device remains undamaged during transport of the magnetic resonance device together with the cable transport carrier facility 20. After transport of the magnetic resonance device together with the cable transport carrier facility 20 this is dismantled from the magnetic resonance device.

Alternate exemplary embodiments of the cable transport carrier facility 70 are shown in FIGS. 7 through 10. Components, features and functions which remain substantially the same are basically labeled with the same reference characters. The description below is substantially restricted to the differences from the exemplary embodiment depicted in FIG. 1 through 6, in which case, as regards components, features and functions which remain the same, the reader is referred to the description of the exemplary embodiment in FIG. 1 through 6.

Figure 7:
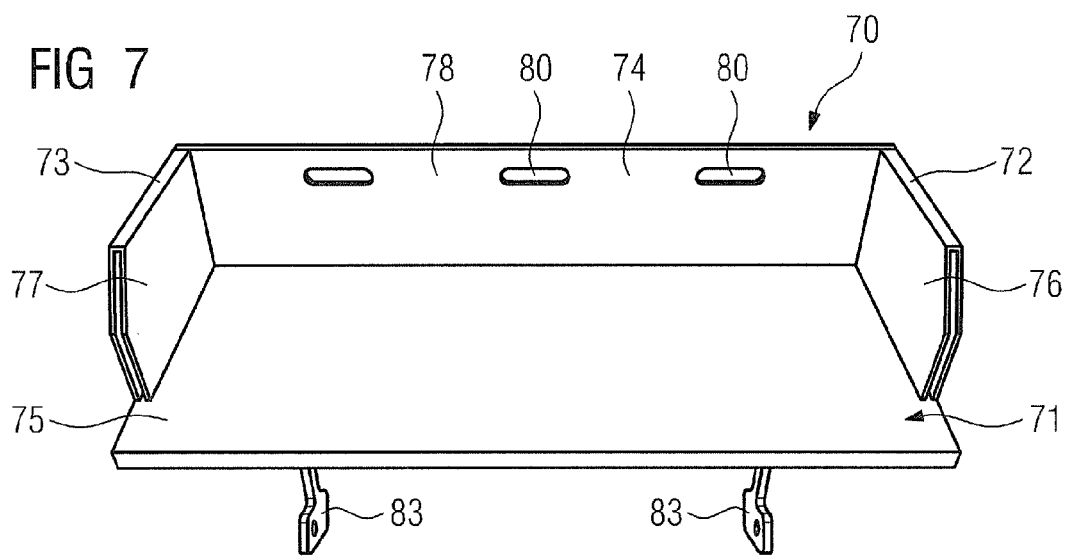
Figure 8:
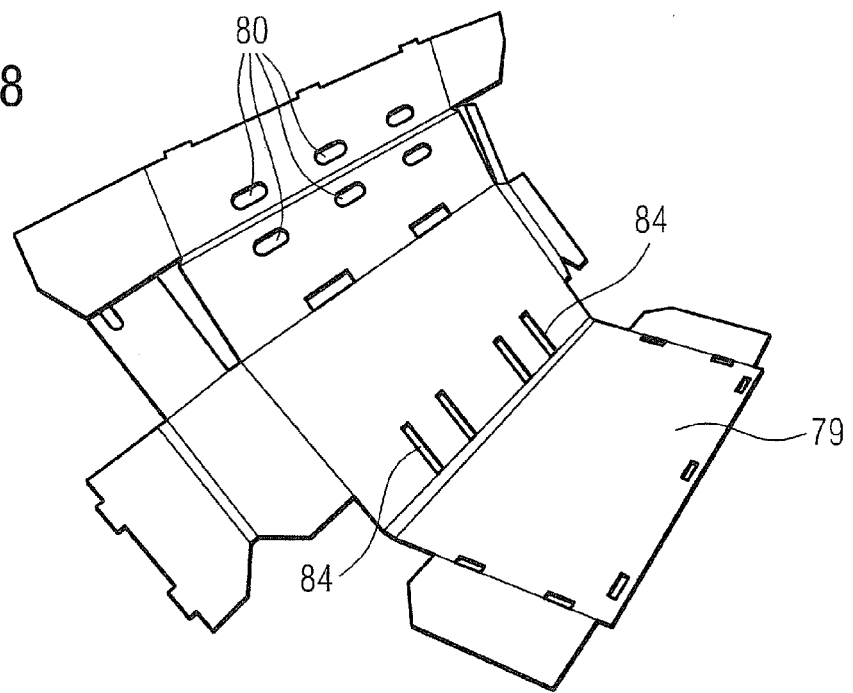
Figure 9:
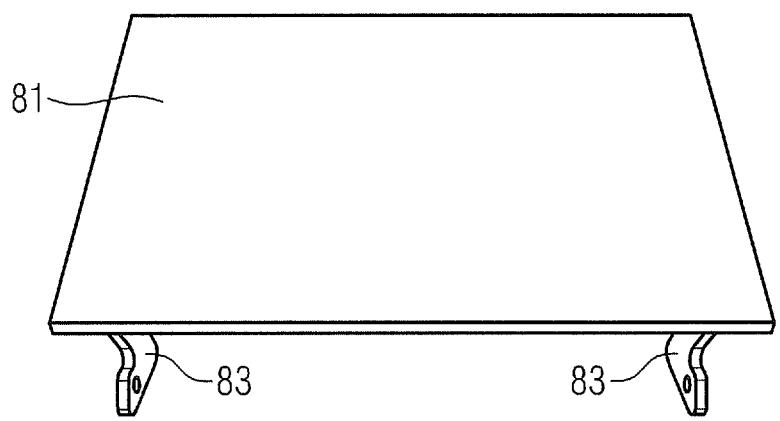
Figure 10:
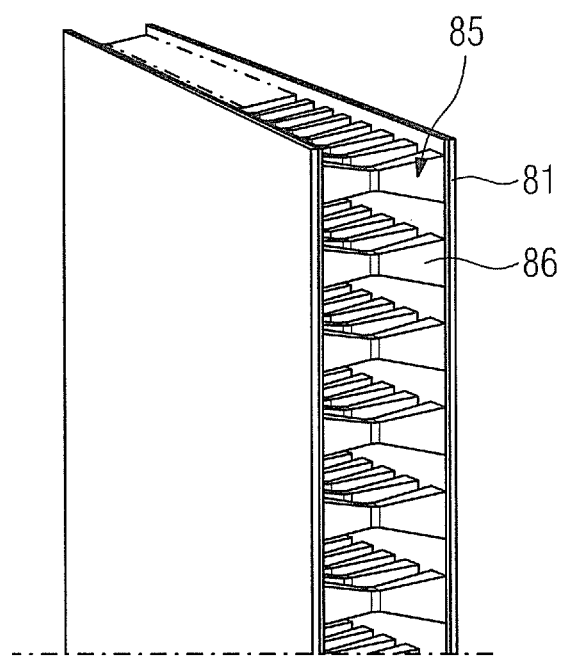

An alternate embodiment of the cable transport carrier facility 70 is shown schematically in FIG. 7. The cable transport carrier facility 70 features a component 75 formed by a floor panel unit 71 and three components 76, 77, 78 each formed by a wall element 72, 73, 74, with the wall elements 72, 73, 74 being embodied in one piece at least partly with the floor panel unit 71. For this purpose the cable transport carrier facility 70 comprises a folding carton 79 (FIG. 8). Folded up, the folding carton 79 forms the three wall elements 72, 73, 74 and partly the floor panel unit 71. The three wall elements 72, 73, 74 are embodied with multiple walls because of the folding of the folding carton 79. Cutouts 80 are also embossed and/or stamped into the folding carton 79, so that the folded-up folding carton 79 has cutouts 80 in the wall elements 72, 73, 74 which can be used for attaching system cables and together with a surround of the cutouts 80, can be used as grip elements.

For stabilization of the floor panel unit 25 this features a floor panel element 81 (FIG. 9) which is made of wood. This floor panel element 81 is placed on the folding carton 79 before folding of the folding carton to produce the cable transport carrier facility 20 and subsequently the folding carton 79 is folded to form the wall elements 72, 73, 74 and the floor panel unit 25. In this way the floor panel element 81 is directly surrounded by the carton walls of the folding carton 79 and together with these forms the floor panel unit 25.

Also arranged on the floor panel element 81 are two support units 83, which are embodied in a similar way to that described for FIGS. 1 through 6. The two support units 83 are attached to the floor panel element 81. The folding carton 79 already has pre-stamped cutouts 84 for this purpose through which the two support units 83 are passed when the folding carton 79 is folded, so that these project out of the folded folding carton 79 after provision of the floor panel unit 25.

As an alternative to a floor panel element 81 made of wood, this element can also be made of a polymer plastic with a support structure 85 for example. This is shown by way of example in FIG. 10. The support structure 85 in the present exemplary embodiment is made of two layers of pyramid shape embossed support elements 86, which are welded to one another. These welded pyramids, together with cover layers of the floor panel element 81, form a stable sandwich construction. For a stabilization of the floor panel element 81 said construction can feature layer elements which are arranged on two opposing sides of the support structure 85 facing outwards, so that the support structure 85 is arranged between the layer elements. In this way a pressure especially acting on the floor panel element 81 at a particular point and or a force acting at a particular point can be distributed to the entire floor panel element. The floor panel element can be formed in this case from a raster core panel and/or further components appearing sensible to the person skilled in the art, which are especially made of light sandwich materials for example.

As an alternative or in addition to the floor panel element 81, it is also conceivable for at least one of the wall elements 72, 73, 74, to increase rigidity and/or increase stability of the cable transport carrier facility 70, to be provided with a wooden element and/or a component with a support structure 85. There can further be provision for the complete floor panel unit 71 and/or at least one of the wall elements 72, 73, 74 to be formed entirely from a component with a support structure 85.

The invention claimed is:

1. A cable transport carrier facility for transporting a system cable of a medical imaging facility, comprising:
   a component that is made at least partly of an organic material;
   a floor panel unit for accommodating the system cable;
   a support unit for supporting the cable transport carrier facility on the medical imaging facility,
   wherein the support unit comprises a base element, a first fitting element embodied in one piece with the base element, and a second fitting element for attaching the support unit to the floor panel unit,
   wherein the first fitting element is arranged on an outer surface of the floor panel unit facing away from an area for accommodating the system cable,
   wherein the second fitting element is arranged on an opposing outer surface of the floor panel unit facing towards the area for accommodating the system cable,
   wherein the first fitting element and the second fitting element each have holes extending traverse to a contact surface of the first fitting element and the second fitting element,
   wherein the first fitting element and the second fitting element are attached to the floor panel unit by screws routed through the holes, and
   wherein the second fitting element comprises a hook for attaching the system cable.

2. The cable transport carrier facility as claimed in claim 1, wherein the component is made at least partly of a material containing cellulose.

3. The cable transport carrier facility as claimed in claim 1, wherein the component comprises a support structure that is made at least partly of the organic material.

4. The cable transport carrier facility as claimed in claim 1, wherein the floor panel unit comprises a cutout.

5. The cable transport carrier facility as claimed in claim 1, wherein the component comprises a wall element for accommodating the system cable,
   wherein the wall element is arranged substantially perpendicular to the floor panel unit, and
   wherein the wall element comprises a further cutout.

6. The cable transport carrier facility as claimed in claim 1, wherein the base element is embodied substantially in a T shape, and wherein the base element comprises a cutout.

7. The cable transport carrier facility as claimed in claim 1, wherein the support unit is made at least partly of a metal.

8. The cable transport carrier facility as claimed in claim 1, wherein the support unit is embodied in a web shape.

9. A medical examination system, comprising:
   a medical imaging facility to be transported to an examination location for performing a medical examination; and a cable transport carrier facility installed on the medical imaging facility for transporting a system cable of the medical imaging facility;

a floor panel unit for accommodating the system cable;

a support unit for supporting the cable transport carrier facility on the medical imaging facility, wherein the support unit comprises a base element, a first fitting element embodied in one piece with the base element, and a second fitting element for attaching the support unit to the floor panel unit, wherein the first fitting element is arranged on an outer surface of the floor panel unit facing away from an area for accommodating the system cable, wherein the second fitting element is arranged on an opposing outer surface of the floor panel unit facing towards the area for accommodating the system cable, wherein the first fitting element and the second fitting element each have holes extending traverse to a contact surface of the first fitting element and the second fitting element, wherein the first fitting element and the second fitting element are attached to the floor panel unit by screws routed through the holes, and wherein the second fitting element comprises a hook for attaching the system cable.

10. The cable transport carrier facility as claimed in claim 1, wherein the support unit is supported on a main magnet surrounded by a housing shell of the medical imaging facility so that the housing shell of the medical imaging facility remains undamaged during transporting the system cable of the medical imaging facility.

* * * * *